United States Patent [19]

Walker et al.

[11] Patent Number: 4,587,964
[45] Date of Patent: May 13, 1986

[54] RASP TOOL

[75] Inventors: Charles B. Walker; Roy Y. Hori; Michael B. Butler, all of Warsaw, Ind.

[73] Assignee: Zimmer, Inc., Warsaw, Ind.

[21] Appl. No.: 698,464

[22] Filed: Feb. 5, 1985

[51] Int. Cl.[4] ............................................. A61F 5/04
[52] U.S. Cl. ................................... 128/92 E; 128/305
[58] Field of Search ............ 128/92 E, 92 EC, 92 R, 128/305, 305.1, 317, 303 R

[56] References Cited

U.S. PATENT DOCUMENTS

| D. 272,648 | 2/1984 | Bolesky et al. | D24/28 |
| D. 273,806 | 5/1984 | Bolesky et al. | D24/28 |
| 3,147,750 | 9/1964 | Fry | 128/303 R |
| 3,667,456 | 6/1972 | Charnley | 128/92 E |
| 3,815,599 | 6/1974 | Deyerle | 128/92 E |
| 3,874,003 | 4/1975 | Moser et al. | 3/1 |
| 4,298,074 | 11/1981 | Mattchen | 128/303 R |
| 4,306,550 | 12/1981 | Forte | 128/92 E |
| 4,319,577 | 3/1982 | Bofinger et al. | 128/303 R |
| 4,399,813 | 8/1983 | Barber | 128/92 EC |
| 4,466,429 | 8/1984 | Loscher et al. | 128/92 E |
| 4,467,801 | 8/1984 | Whiteside | 128/92 E |

OTHER PUBLICATIONS

"The PCA Total Hip System", Howmedica, 1984, pp. 16, 15, 42, and 43.
"Link Calcar Reamer DBGM", W. Link, 1983.

Primary Examiner—Gene Mancene
Assistant Examiner—C. W. Shedd
Attorney, Agent, or Firm—Paul D. Schoenle

[57] ABSTRACT

A rasp tool comprises a handle and a cutter. The handle carries a releasable locking assembly to couple the cutter to the handle and the releasable locking assembly is compactly arranged at one end of the handle via a transversely extending flange which also acts as a spacer between the releasable locking assembly and the roughened outer surface of the cutter.

14 Claims, 5 Drawing Figures

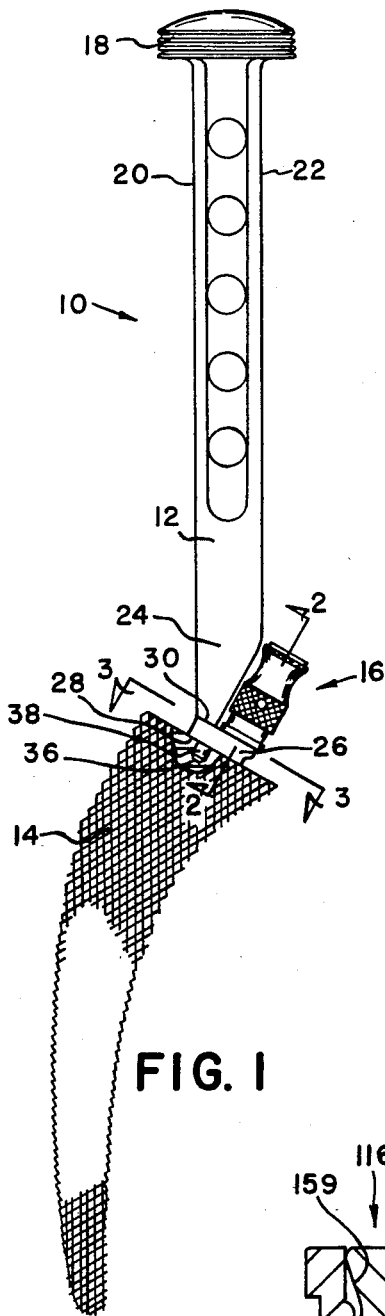
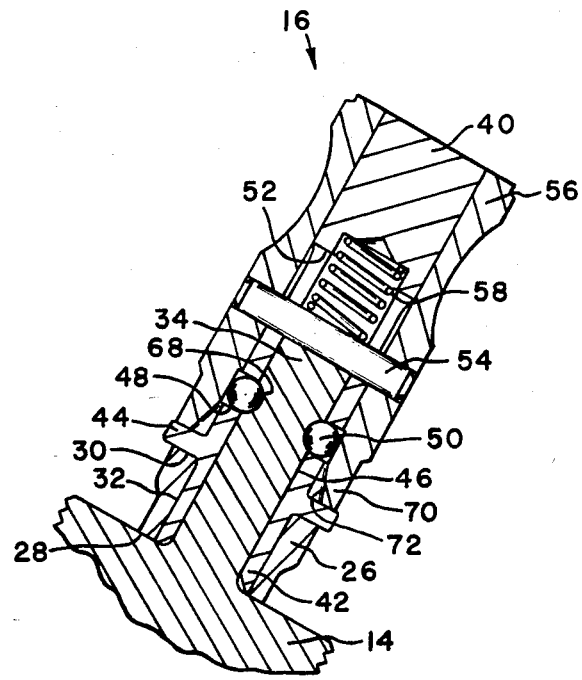
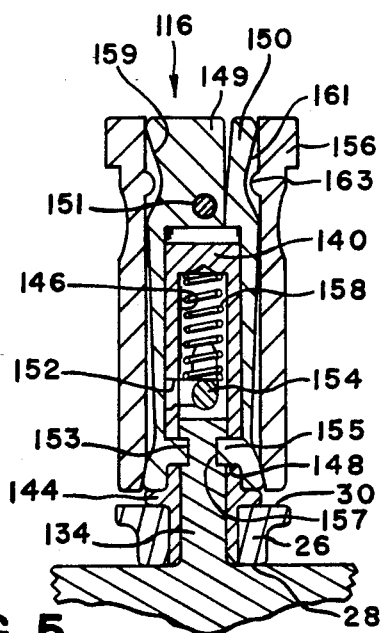
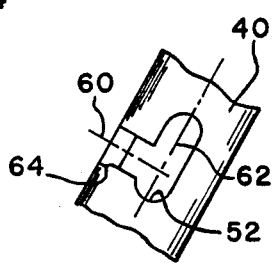
FIG. 1
FIG. 2
FIG. 3
FIG. 4
FIG. 5

RASP TOOL

The present invention relates to a rasp tool which is used by a surgeon to contour a bone or the like. More specifically, the rasp tool is used where a femoral prosthesis is implanted in a femur.

It has been proposed to utilize a rasp tool with a handle that is releasable relative to a cutter so that the cutter can remain lodged in the femur to enable further contouring of the proximal end of the femur as well as provisional sizing of a ball in the acetabular socket. Such a rasp tool is shown in U.S. Pat. No. 4,306,550, Mark R. Forte, issued Dec. 22, 1981. These tools disclose releasable chucks which are directly facing the cutter so that fluids and bone particles are easily disposed on the release mechanism to hinder reliable latching and release during surgery. Additional rasp tools include complicated locking arms for coupling the cutter to the handle and these tools are cumbersome to operate.

The present invention teaches a simple releasable locking assembly for a rasp tool which disposes the releasable locking assembly on the handle to reduce contact with bone particles while also providing a compact structure facilitating finger operation during surgery. To this end, the present invention covers a rasp tool for contouring a bone or the like comprising a handle with a head at one end and a releasable locking assembly at the other end, a cutter cooperating with the releasable locking assembly and adapted to contour the bone, the other end including a transversely extending flange defining a pair of oppositely facing surfaces, the cutter engaging one of the surfaces when cooperating with the releasable locking assembly and the releasable locking assembly extending away from the other surface and defining a length which is substantially less than a length for the handle, the flange defining an aperture for receiving a portion of the cutter and the portion extends into the releasable locking assembly to cooperate therewith, and the releasable locking assembly is carried by the flange on one side of the latter to remain spaced from all of the cutter except for that portion of the cutter extending into the aperture.

It is an object of the present invention to provide a compact and simple releasable locking assembly which is strategically disposed on a rasp tool handle to reduce intimate contact with bone particles removed by a cutter.

In the drawings accompanying this application,
FIG. 1 is a side view of the rasp tool of the present invention.
FIG. 2 is a cross sectional view taken along line 2—2 of FIG. 1.
FIG. 3 is a cross sectional view taken along lines 3—3 of FIG. 1.
FIG. 4 is a side view of a support showing an opening therethrough.
FIG. 5 is a view similar to FIG. 2 showing an alternative embodiment of the present invention.

A rasp tool 10 includes a handle 12 and a cutter 14 releasably coupled thereto by means of a releasable locking assembly 16. The handle 12 forms a head 18 at one end remote from the cutter 14. A pair of edges 20 and 22 extend from the head in a parallel direction to a tapered end 24. At the tapered end 24, the one edge 22 changes direction to approach the other edge 20. The tapered end terminates in a flange 26 extending transversely to the one edge 22 to define one surface 28 facing the cutter 14 and another surface 30 facing the releasable locking assembly 16. The flange 26 is apertured at 32 to receive a stem 34 of the cutter 14 while the cutter includes a blind bore 36 to receive a post 38 extending outwardly from the handle 12.

Turning to FIG. 2, the releasable locking assembly 16 includes a support 40 with one end 42 disposed in the aperture 32 so that a shoulder 44 is secured via welding or other suitable means to the surface 30 of flange 26. The support 40 forms a bore 46 to receive the stem 34. A first pair of openings 48 receive balls 50 and a second pair of openings 52 receive a key 54. The key 54 is secured to a sleeve 56 to move therewith relative to the support 40 and the key 54 extends through the bore 46 so that a spring 58 carried in the bore 46 extends from the support 40 to the key to bias the key and sleeve toward the flange 26. The openings 52 are provided with a lateral arcuate axis 60 and a longitudinal axis 62, see FIG. 4, so that the key 54 and sleeve 56 will be locked longitudinally when the key is in the lateral axis. Rotation of the sleeve and key to align the latter with the longitudinal axis permits the sleeve and key to move away from the flange 26 against the force of spring 58 for a purpose to be defined hereinafter. The lateral arcuate axis is provided with a slight notch 64 remote from the longitudinal axis 62 to receive the key 54 when the latter is disposed in a locked position to maintain the balls 50 disposed in the support openings 48 and also disposed in an arcuate groove 68 formed on the end of stem 34.

In the position illustrated in FIG. 2, the cutter 14 is locked to the handle. This follows from the key 54 being disposed in the lateral axis 60 so that the sleeve 56, which is connected to the key 54, overlaps the balls 50 to prevent withdrawal thereof from the stem groove 68. Consequently, the balls 50 form an interface with the stem 34 to prevent withdrawal. In order to release the handle from the cutter, the sleeve 56 is rotated to align the key 54 with the longitudinal axis of openings 52 and, then the sleeve is pulled away from the flange 26 against the force of spring 58. Movement of the sleeve aligns an end 70 of the sleeve with the balls 50. The end 70 includes a tapered relief 72 permitting the balls to move radially outwardly, thereby freeing the stem relative the releasable locking assembly 16 so that the handle 12 and releasable locking assembly 16 can be separated from the cutter 14.

In the alternative embodiment of FIG. 5 similar parts are identified with the same reference numerals as in FIG. 2 plus one hundred. The releasable locking assembly 116 includes a support 140 fixedly coupled to the flange 26 of the handle. The support 140 includes a shoulder 144 facing a surface 30 of flange 26 and a bore 146 receiving a stem 134, a spring 158 and a key 154. The key 154 is fastened to the sleeve 156 so that the spring 158 biases the key 154 and the sleeve 156 toward the flange 26. The support 140 includes openings 152 to receive the key 154. A pair of tabs 149 and 150 are pivotally carried by a pin 151. The tabs extend toward the flange 26 and define stops 153, 155 extending through openings 148 on the support. The stops 153, 155 in the locked position shown fit within a recess 157 on the stem 134. The tabs 149, 150 are flared outwardly adjacent the shoulder 144 so that the sleeve 156 engages the tabs to retain the stops 153, 155 in the recess 157. The tabs 149, 150 include depressions 159, 161 aligned with a ridge 163 when the sleeve 156 retains the stops 153, 155 in the stem recess 157. To release the stem the sleeve is rotated and then moved away from the shoulder 144 so that the ridge 163 engages the tabs 149, 150 above the pin 151 to move the stops 153, 155 away from each other, thereby withdrawing the latter from the stem recess 157 to permit separation between the cutter and the handle.

In view of the foregoing description the releasable locking assembly 16, 116 is compactly arranged at the tapered end 24 of the handle on one side of the flange 26. Consequently, the handle 12 can be tightly gripped by a surgeon without any interference by the releasable locking assembly 16 or 116. Furthermore, the cutter 14 with its roughened outer suface is spaced from the releasable locking assembly 16, 116 by the flange 26 so that only the stem thereof contacts the releasable locking assembly 16, 116. Therefore, bone particles, fluids and/or tissue covering the cutter, after utilization of the same, will be substantially spaced from the releasable locking assembly 16, 116 to reduce the chance of jamming the assembly.

We claim:

1. A rasp tool for contouring a bone or the like comprising a handle with a head at one end and a releasable locking assembly at the other end, a cutter cooperating with the releasable locking assembly and adapted to contour the bone, the other end including a transversely extending flange defining a pair of oppositely facing surfaces, the cutter engaging one of the surfaces when cooperating with the releasable locking assembly and the releasable locking assembly extending away from the other surface and defining a length which is substantially less than a length for the handle, the flange defining an aperture for receiving a portion of the cutter and the portion extends into the releasable locking assembly to cooperate therewith, and the releasable locking assembly is carried by the flange on one side of the latter to remain spaced from all of the cutter except for that portion of the cutter extending into the aperture.

2. The rasp tool of claim 1 in which the releasable locking assembly includes a support fixedly coupled to the flange and a sleeve movably carried by the support in spaced relation to the flange and the handle.

3. The rasp tool of claim 2 in which the support extends into the aperture.

4. The rasp tool of claim 2 in which the support includes a shoulder engageable with the other surface and the sleeve is resiliently biased toward the shoulder.

5. The rasp tool of claim 2 in which the support defines a bore for receiving the portion of the cutter, a first opening receiving a key carried by the sleeve and a second opening receiving a stop cooperating with the portion of the cutter to selectively prevent withdrawal of the latter.

6. The rasp tool of claim 5 in which a spring is disposed in the support bore between the key and the support.

7. The rasp tool of claim 1 in which the releasable locking assembly is movable along an axis extending outwardly from the other surface and the releasable locking assembly is also rotatable about the axis.

8. The rasp tool of claim 1 in which the other surface is substantially circular in shape and the releasable locking assembly defines a cylindrical outer profile with a diameter substantially equal to or greater than a diameter for the circular other surface.

9. The rasp tool of claim 1 in which the handle defines a pair of edges extending from the head to the other end, the edges are parallel from the head to but not including the other end, one of the edges changing directions at the other end to approach the other edge which is linear from the head to the flange, and the releasable locking assembly is carried by the flange adjacent to but slightly spaced from that portion of the one edge which is approaching the other edge.

10. The rasp tool of claim 9 in which the length of the releasable locking assembly is substantially equal to a length defined by that portion of the one edge approaching the other edge.

11. The rasp tool of claim 1 in which the releasable locking assembly comprises a support fixedly coupled to the flange, a sleeve movable relative to the support, and at least one tab cooperating with the sleeve to prevent separation of the cutter from the flange in a first position, the sleeve being movable to positively reposition the tab so as to permit separation between the cutter and the handle in a second position, the support defining an opening and the tab defining a stop extending into the opening to engage the portion of the cutter in the first position.

12. The rasp tool of claim 11 in which the tab is pivotally carried by the support at an end of the latter spaced from the flange.

13. A rasp tool for contouring a bone comprising a handle with a head at one end and a releasable locking assembly at the other end, a rasp element cooperating with the releasable locking assembly and adapted to contour the bone, the other end of the handle defining a transversely extending flange to substantially dispose the releasable locking assembly on one side of the flange, the flange defining an opening for receiving a stem portion of the rasp element and the stem portion extending through the flange opening to cooperate with the releasable locking assembly solely on the one side of the flange, and the remaining portion of the rasp element is disposed on the other side of the flange.

14. A rasp tool for contouring a bone comprising a handle with a head at one end and a releasable locking assembly at the other end, a rasp element cooperating with the releasable locking assembly for selective attachment to an separation from the handle, the other end of the handle including a transversely extending flange with a pair of oppositely facing surfaces, the rasp element extending outwardly from one of the surfaces when attached to the handle, the releasable locking assembly extending outwardly from the other surface and the handle intersects the flange on the other surface for connection therewith at a location transversely disposed from the releasable locking assembly whereby the handle and releasable locking assembly extend outwardly from the other surface substantially in the same direction.

* * * * *